United States Patent
Yi et al.

(10) Patent No.: US 11,534,392 B2
(45) Date of Patent: Dec. 27, 2022

(54) COSMETIC COMPOSITION COMPRISING EXOSOMES DERIVED FROM GALACTOMYCES AS ACTIVE INGREDIENT

(71) Applicant: ExoCoBio Inc., Seoul (KR)

(72) Inventors: Yong Weon Yi, Seoul (KR); Byong Seung Cho, Gunpo-si (KR)

(73) Assignee: ExoCoBio Inc., Seoul (KR)

(*) Notice: Subject to any disclaimer, the term of this patent is extended or adjusted under 35 U.S.C. 154(b) by 89 days.

(21) Appl. No.: 17/171,399

(22) Filed: Feb. 9, 2021

(65) Prior Publication Data

US 2021/0161798 A1 Jun. 3, 2021

Related U.S. Application Data (63) Continuation of application No. PCT/KR2019/010533, filed on Aug. 20, 2019.

(30) Foreign Application Priority Data

Sep. 6, 2018 (KR) .................. 10-2018-0106747
Jan. 29, 2019 (KR) .................. 10-2019-0011047

(51) Int. Cl.
*A61K 8/9728* (2017.01)
*A61K 8/02* (2006.01)
*A61Q 19/02* (2006.01)
*A61Q 19/08* (2006.01)

(52) U.S. Cl.
CPC .......... *A61K 8/9728* (2017.08); *A61K 8/0212* (2013.01); *A61Q 19/02* (2013.01); *A61Q 19/08* (2013.01)

(58) Field of Classification Search
CPC ......... A61K 8/9728; A61K 8/14; A61Q 19/00
See application file for complete search history.

(56) References Cited

U.S. PATENT DOCUMENTS

| | | | |
|---|---|---|---|
| 2011/0262025 A1* | 10/2011 | Jarrold | A61Q 19/08 506/7 |
| 2014/0318565 A1* | 10/2014 | Ito | A45D 44/22 132/319 |
| 2017/0152484 A1 | 6/2017 | Cho et al. | |
| 2017/0209365 A1 | 7/2017 | Cho et al. | |

FOREIGN PATENT DOCUMENTS

| | | | | |
|---|---|---|---|---|
| CN | 107519104 A | * | 12/2017 | ............ A61K 8/02 |
| JP | 2017-534629 A | | 11/2017 | |
| KR | 10-2014-0066456 A | | 6/2014 | |
| KR | 10-2015-0099457 A | | 8/2015 | |
| KR | 10-2016-0055682 A | | 5/2016 | |
| KR | 10-2017-0127793 A | | 11/2017 | |
| KR | 10-2018-0003344 A | | 1/2018 | |
| WO | 2019/088656 A1 | | 5/2019 | |
| WO | WO-2019088656 A1 | * | 5/2019 | ........... A61K 31/728 |

OTHER PUBLICATIONS

CN-107519104-A (Espacenet English translation, downloaded Jun. 2022) (Year: 2022).*
Minji Lee et al., "The Effects of Essence-Formed Cosmetic Ingredients Containing the Galactomyces Ferment Filtrate on Skin Improvements in Keratinization, Pores, Sebum Excretion, Brightness and Acne", Kor.J. Aesthet. Cosmetol., Feb. 2014, pp. 77-84, vol. 12, No. 1.
International Search Report for PCT/KR2019/010533 dated Nov. 25, 2019 (PCT/ISA/210).
Masaru Kadota et al., "Forefront of extracellular vesicle / exosome research: aiming for clinical English application", Journal of Japanese Pharmacology, 2017, vol. 149, No. 3, pp. 119-122 (7 pages total).

* cited by examiner

*Primary Examiner* — Mark V Stevens
(74) *Attorney, Agent, or Firm* — Sughrue Mion, PLLC (57) ABSTRACT

A cosmetic composition including exosomes derived from *Galactomyces* as an active ingredient is provided for skin regeneration, skin elasticity improvement or skin wrinkle reduction. The cosmetic composition has excellent effects on skin regeneration, skin elasticity improvement and/or skin wrinkle reduction.

14 Claims, 9 Drawing Sheets
(1 of 9 Drawing Sheet(s) Filed in Color)

COSMETIC COMPOSITION COMPRISING EXOSOMES DERIVED FROM GALACTOMYCES AS ACTIVE INGREDIENT

CROSS REFERENCE

This application is a Bypass Continuation of International Application No. PCT/KR2019/010533 filed Aug. 20, 2019, claiming priority based on Korean Patent Application No. 10-2018-0106747 filed Sep. 6, 2018 and Korean Patent Application No. 10-2019-0011047 filed Jan. 29, 2019, the entire contents of which are incorporated herein by reference.

TECHNICAL FIELD

The present invention relates to a cosmetic composition for skin regeneration, skin elasticity improvement and skin wrinkle reduction comprising exosomes derived from *Galactomyces* as an active ingredient.

BACKGROUND ART

It is known that skin aging leads to a decrease in skin elasticity and an increase in skin wrinkles and that the decrease in skin elasticity and the formation of skin wrinkles occur due to decreased synthesis of collagen and stimulated expression of the collagenase matrix metalloproteinase (MMP).

In addition, it is known that in skin cells, COX-2, an enzyme that produces inflammatory cytokines increases due to aging progression or ultraviolet (UV) rays, resulting in increased synthesis of prostaglandin E2 and increased production of inflammation inducers. Due to inflammatory reactions, the biosynthesis of MMP increases, causing collagen degradation and resulting in the decrease in skin elasticity and the formation of skin wrinkles. In particular, when sunlight and ultraviolet rays are irradiated directly onto skin, a lot of free radicals are generated, and these free radicals could damage the antioxidant defense system of skin, thus increasing wrinkles, making skin loose and accelerating skin aging. Therefore, in order to reduce skin wrinkles and to maintain elasticity, it is necessary to protect skin by inhibiting the production of reactive oxygen species and free radicals, inhibiting inflammatory responses and encouraging skin regeneration from wounds.

Substances known to be effective in reducing skin wrinkles include adenosine and retinoic acid. However, adenosine has little efficacy in clinical practice, and retinoic acid cannot be used for pregnant women and has side effects such as erythema. Accordingly, functional cosmetics for anti-aging skin containing active ingredients derived from plants or natural products have recently attracted attention. However, functional cosmetics containing plant extracts as an active ingredient have problems that they may cause a foreign body sensation during their evaporation after application to the skin, and the duration of the effect thereof is short.

Recently, there have been reports that cell secretomes contain various bioactive molecules that regulate cellular behaviors. In particular, cell secretomes contain 'exosome' that has intercellular signaling functions, and thus studies on the components and functions thereof have been actively conducted.

Cells release various membraneous vesicles to their extracellular environment, and these released vesicles are usually called extracellular vesicles (EVs). The EV is also called cell membrane-derived vesicle, ectosome, shedding vesicle, microparticle, exosome, etc., and is also used discriminately from exosome in some cases.

Exosome is a vesicle of tens to hundreds of nanometers in size, which consists of a phospholipid bilayer membrane having the same structure as that of the cell membrane. This exosome contains proteins, nucleic acids (mRNA, miRNA, etc.) and the like which are called exosome cargo. It is known that exosome cargo includes a wide range of signaling factors, and these signaling factors are specific for cell types and regulated differently depending on secretory cells' environment. It is known that exosome is an intercellular signaling mediator secreted by cells, and various cellular signals transmitted through it regulate cellular behaviors, including the activation, growth, migration, differentiation, dedifferentiation, apoptosis, and necrosis of target cells. Exosome contains specific genetic materials and bioactive factors depending on the nature and state of cells from which the exosome was derived. Exosome derived from proliferating stem cells regulates cell behaviors such as cell migration, proliferation and differentiation, and recapitulates the function of stem cells involved in tissue regeneration (Nature Review Immunology 2002 (2) 569-579).

Exosomes called "avatars" of cells are known to be released not only from stem cells and cancer cells, but also from cells of various organisms such as plants, bacteria, fungi, and algae. For example, exosomes may be isolated from conditioned media or fermentation products of yeast, as well as conditioned media of mesenchymal stem cells and conditioned media of fibroblasts.

Yeast is used in the manufacture of various fermented foods, and it is known that yeast fermentation products obtained in processes of brewing alcoholic beverages have an effect on skin condition improvement. However, studies on the isolation, purification and characterization of exosomes derived from yeast remain insufficient. Therefore, more detailed characterization and functional studies of exosomes derived from yeast are required.

In this regard, fermented cosmetics have recently gained popularity, and the types of yeast used in cosmetics have also increased. There are approximately hundreds of types of yeast used as cosmetic ingredients, and among the fermented cosmetic ingredients, a *Galactomyces* ferment filtrate is receiving the best consumer response. *Galactomyces* is a genus of yeast found in the process of researching various yeasts, focusing on the fact that the skin of the hand of the craftsman who brews refined rice wine is elastic and clean for his age. The *Galactomyces* ferment filtrate is rich in vitamins, minerals, amino acids, organic acids, enzymes, yeast peptides and the like. However, the *Galactomyces* ferment filtrate may cause side effects such as skin troubles, skin redness, or dermatitis in people whose skin is sensitive to fermented ingredients.

The present inventors have found that exosomes derived from *Galactomyces* are effective in skin regeneration, skin elasticity improvement and/or skin wrinkle reduction, etc., and have developed a cosmetic composition for skin regeneration, skin elasticity improvement or skin wrinkle reduction, comprising exosomes derived from *Galactomyces* as an active ingredient.

Meanwhile, it is to be understood that the matters described as the background art are intended merely to aid in the understanding of the background of the present invention and are not admitted as prior art against the present invention.

SUMMARY OF INVENTION

An object of the present invention is to provide a cosmetic composition for skin regeneration, skin elasticity improvement or skin wrinkle reduction comprising exosomes derived from *Galactomyces* as an active ingredient.

However, the objects of the present invention as described above are illustrative and the scope of the present invention is not limited thereby. In addition, other objects and advantages of the present invention will be more apparent from the following description, the appended claims and the accompanying drawings.

DETAILED DESCRIPTION OF INVENTION

The present invention provides a cosmetic composition for skin regeneration, skin elasticity improvement or skin wrinkle reduction comprising exosomes derived from *Galactomyces* (*Galactomyces*-derived exosomes) as an active ingredient.

As used herein, the term "*Galactomyces*" is a genus of fungi in the family Dipodascaceae, and refers to yeasts of the genus *Galactomyces*, which are used in brewing or fermentation processes. Various *Galactomyces* strains are known, which are used in the process of brewing alcoholic beverages by fermenting grains.

As used herein, the term "exosomes" refers to nano-sized vesicles secreted or released from yeasts into extracellular spaces and having a membrane structure, and is also referred to as exosome-like vesicles or exosome-like particles.

As used herein, the term "exosomes derived from *Galactomyces* (*Galactomyces*-derived exosomes)" are meant to include all exosomes isolated from conditioned media of *Galactomyces* or *Galactomyces* ferments, or from biological solutions of *Galactomyces* equivalent thereto, or secreted and/or released from *Galactomyces* itself.

As used herein, the term "skin elasticity" refers to a feature in which skin deformed by an external force easily returns to its original shape when the external force is removed. The term "skin wrinkles" refers to fine lines caused by skin aging. Skin wrinkles may be caused by genetic factors, reduction in collagen and elastin present in the skin dermis, external environmental factors, or the like. Accordingly, the term "skin wrinkle reduction or improvement" as used herein refers to suppressing or inhibiting the formation of wrinkles on the skin, or reducing already formed wrinkles.

In a cosmetic composition according to one embodiment of the present invention, the *Galactomyces*-derived exosomes may be isolated from conditioned media of *Galactomyces* or from *Galactomyces* ferments.

The cosmetic composition according to one embodiment of the present invention may be, for example, cream or lotion.

Meanwhile, the cosmetic composition according to one embodiment of the present invention may suitably contain components which are generally used in cosmetic products, for example, moisturizers, antioxidants, oily components, UV absorbers, emulsifiers, surfactants, thickeners, alcohols, powder components, colorants, aqueous components, water, and various skin nutrients, etc., as needed, within the range that does not impair the effect of the present invention.

Furthermore, the cosmetic composition according to one embodiment of the present invention may include, in addition to the *Galactomyces*-derived exosomes, an agent for improving skin condition and/or a moisturizer, which have been used in the prior art, within the range that does not impair the effects (e.g., wrinkle improvement, skin regeneration, skin elasticity improvement, skin beauty, etc.). For example, the *Galactomyces*-derived exosomes of the present invention may be contained in or mixed with at least one of hydrogel, hyaluronic acid, salt of hyaluronic acid (e.g., sodium hyaluronate, etc.), or hyaluronate gel. In the cosmetic composition according to one embodiment of the present invention, the kind of hydrogel is not particularly limited, but the hydrogel may be preferably obtained by dispersing a gelled polymer in a polyhydric alcohol. The gelled polymer may be at least one selected from the group consisting of pluronic, purified agar, agarose, gellan gum, alginic acid, carrageenan, *cassia* gum, xanthan gum, galactomannan, glucomannan, pectin, cellulose, guar gum, and locust bean gum, and the polyhydric alcohol may be at least one selected from the group consisting of ethylene glycol, propylene glycol, 1,3-butylene glycol, isobutylene glycol, dipropylene glycol, sorbitol, xylitol, and glycerin.

The cosmetic composition according to one embodiment of the present invention may be used in various forms, for example, patches, mask packs, mask sheets, creams, tonics, ointments, suspensions, emulsions, pastes, lotions, gels, oils, packs, sprays, aerosols, mists, foundations, powders, and oilpapers. For example, the cosmetic composition may be applied to or soaked in at least one surface of a patch, a mask pack or a mask sheet.

The cosmetic composition is used for the purpose of skin regeneration, skin elasticity improvement, wrinkle improvement and the like, and the cosmetic composition may be prepared as any formulation which is generally prepared in the art. For example, it may be formulated as patch, mask pack, mask sheet, skin softener, nutrition, astringent lotion, nourishing cream, massage cream, eye cream, cleansing cream, essence, eye essence, cleansing lotion, cleansing foam, cleansing water, sunscreen, lipstick, soap, shampoo, surfactant-containing cleanser, bath preparation, body lotion, body cream, body oil, body essence, body cleanser, hairdye, hair tonic, etc., but is not limited thereto.

The cosmetic composition according to one embodiment of the present invention contains components which are commonly used in cosmetic products. For example, the cosmetic composition may contain conventional adjuvants and carriers, such as antioxidants, stabilizers, solubilizers, vitamins, pigments, and fragrances. In addition, other components in each formulation for the cosmetic composition may be suitably selected without difficulty by those skilled in the art depending on the type or intended use of the cosmetic composition.

Another embodiment of the present invention provides a cosmetic method for regulating mammalian skin conditions, except for treatment purposes, using the cosmetic composition. In the cosmetic method of the present invention, the expression "regulating skin conditions" means improving skin conditions and/or prophylactically regulating skin conditions, and the expression "improving skin conditions" means a visually and/or tactilely perceivable positive change in the appearance and feeling of skin tissue. For example, the expression "improving skin conditions" may include skin regeneration, skin elasticity improvement, and/or skin wrinkle reduction.

The cosmetic method according to one embodiment of the present invention includes: (a) applying the cosmetic composition directly to a mammalian skin; or (b) contacting or attaching a patch, a mask pack or a mask sheet, which has the cosmetic composition applied thereto or soaked therein, to the mammalian skin; or sequentially performing (a) and (b). In step (a), the cosmetic composition may be lotion or cream.

Alternatively, the cosmetic method according to one embodiment of the present invention may further comprise (c) removing the patch, mask pack or mask sheet from the mammalian skin after step (b), and applying the cosmetic composition to the mammalian skin. In step (c), the cosmetic composition may be lotion or cream.

In the cosmetic method according to one embodiment of the present invention, the mammal may be humans, dogs, cats, rodents, horses, cattle, monkeys, or pigs.

Advantageous Effects

The cosmetic composition for skin regeneration, skin elasticity improvement or skin wrinkle reduction comprising exosomes derived from *Galactomyces* as an active ingredient according to the present invention has better effects on skin regeneration, skin elasticity improvement and/or skin wrinkle reduction than filtrates of conditioned media of *Galactomyces*. Thus, the cosmetic composition of the present invention has excellent effects on skin regeneration, skin elasticity improvement and/or skin wrinkle reduction.

It should be understood that the scope of the present invention is not limited to the aforementioned effects.

BRIEF DESCRIPTION OF DRAWINGS

The patent or application file contains at least one drawing executed in color. Copies of this patent or patent application publication with color drawing(s) will be provided by the Office upon request and payment of the necessary fee.

EXAMPLES

Hereinafter, the present invention will be described in more detail with reference to the following examples. However, the following examples are only to illustrate the present invention and are not intended to limit or restrict the scope of the present invention. Those that can be easily inferred by those skilled in the art from the detailed description and examples of the present invention are interpreted as falling within the scope of the present invention. References referred to in the present invention are incorporated herein by reference.

Throughout the present specification, it is to be understood that, when any part is referred to as "comprising" any component, it does not exclude other components, but may further include other components, unless otherwise specified.

Example 1: Preparation of *Galactomyces*-Derived Exosomes

*G. candidum* and *G. geotrichum*, which are commercially available *Galactomyces* strains for brewing or fermentation, were shake-cultured, and then the conditioned media were pelleted by centrifugation and the pelleted *Galactomyces* cells were removed.

The supernatants of the conditioned media of *Galactomyces* obtained by the above-described process were filtered through a 0.22-μm filter to remove impurities such as cell debris, waste products and large particles. *Galactomyces*-derived exosomes were isolated from the filtered conditioned media of *Galactomyces* by tangential flow filtration (TFF) method.

Figure 1A:
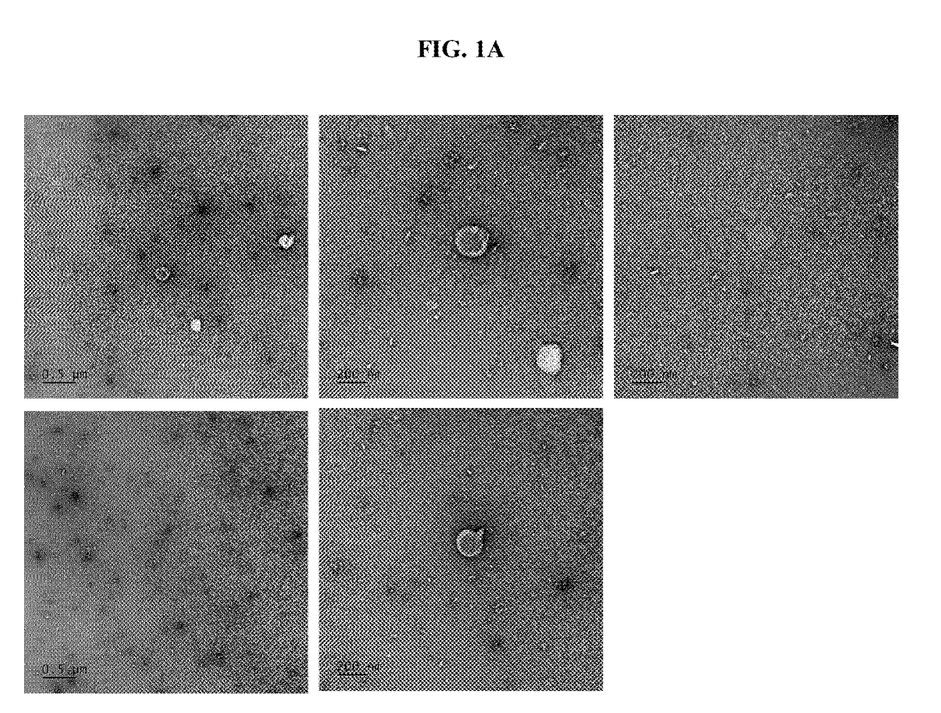
FIG. 1A shows particle images obtained by transmitted electron microscopy (TEM) of *Galactomyces*-derived exosomes obtained according to one embodiment of the present invention.
Figure 1B:
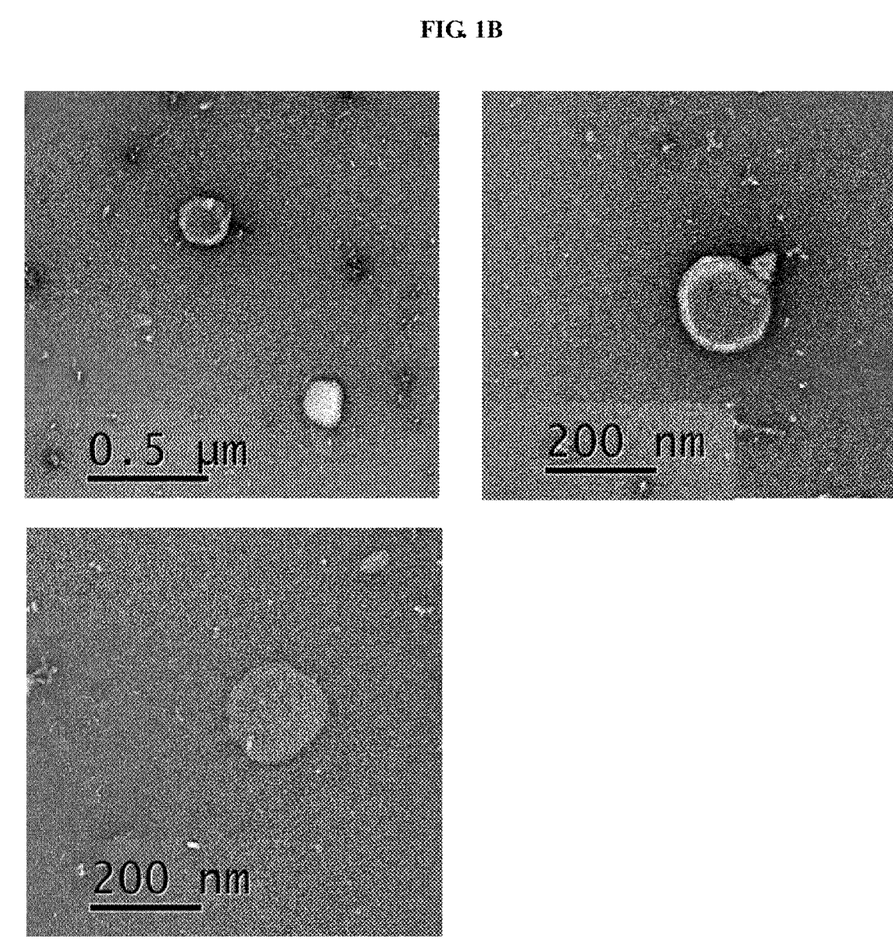
FIG. 1B shows enlarged particle images of FIG. 1A.
Figure 2A:
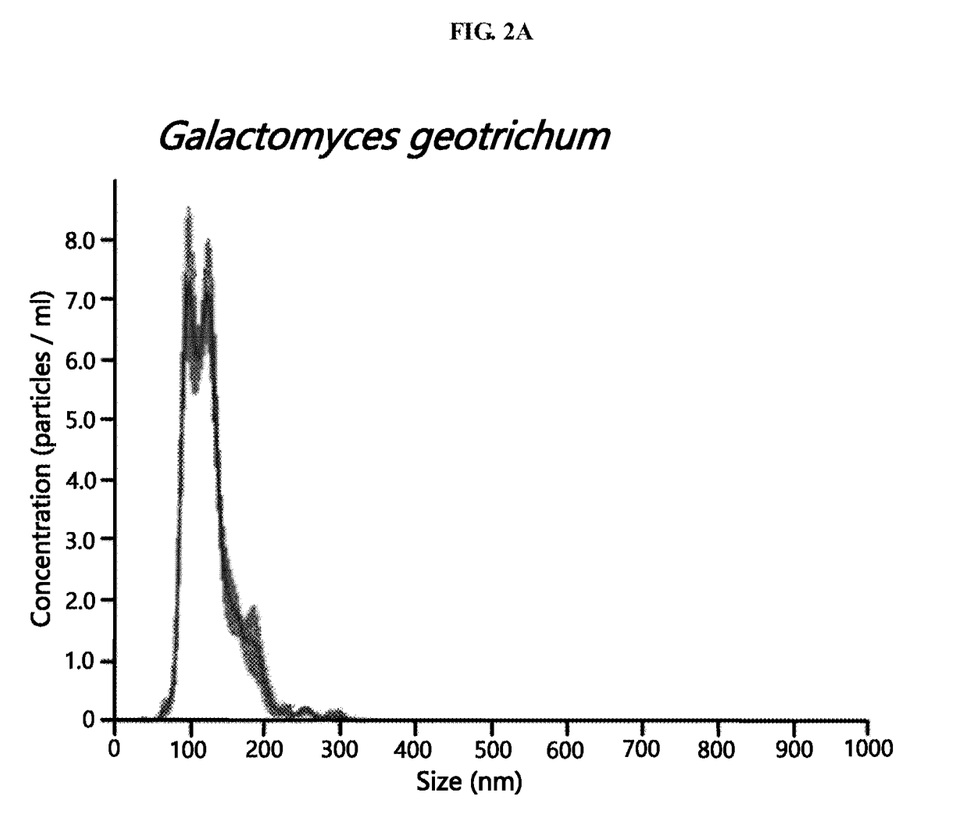
FIGS. 2A and 2B are graphs showing the results of NTA analysis of *Galactomyces*-derived exosomes.
Figure 2B:
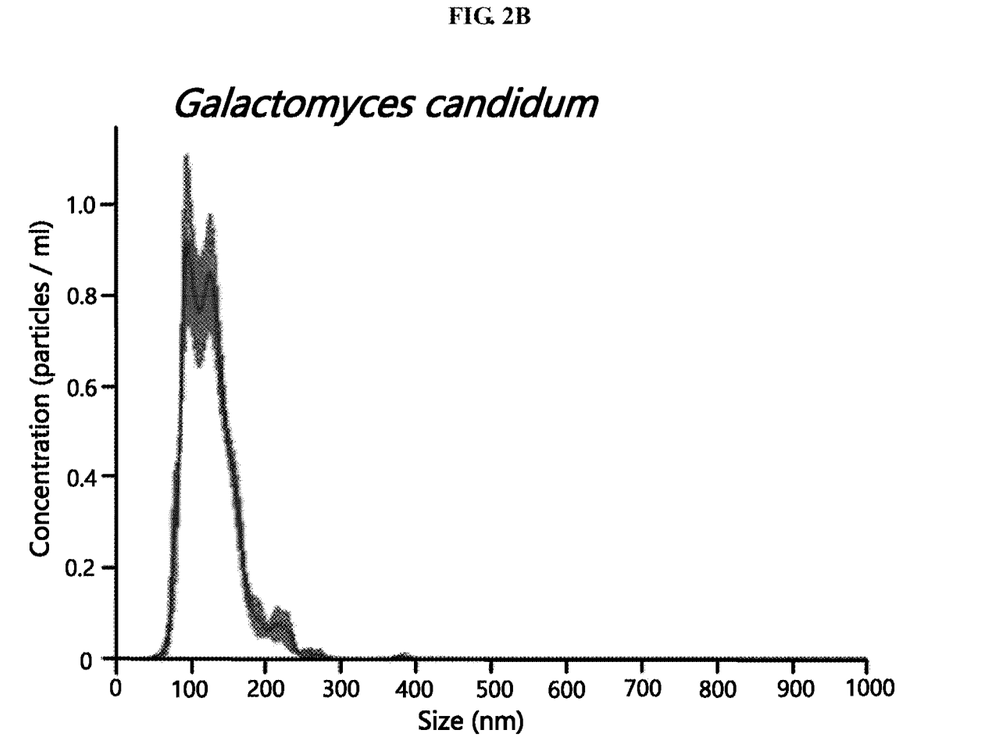

The size of the isolated *Galactomyces*-derived exosomes was analyzed by transmitted electron microscopy (TEM). As shown in FIGS. 1A and 1B, it was confirmed that the isolated *Galactomyces*-derived exosomes were nano-sized vesicles. The size and concentration of the *Galactomyces*-derived exosomes were analyzed by nanoparticle tracking analysis (NTA) using NS300 (purchased from Malvern Panalytical) (FIGS. 2A and 2B).

Figure 3:
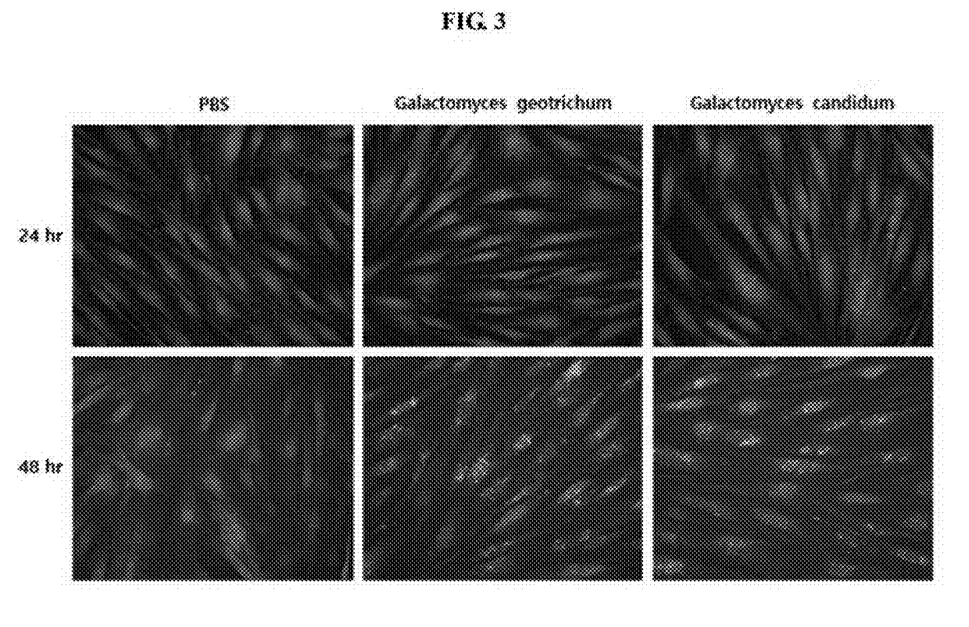
FIG. 3 depicts fluorescence microscopic images of cells showing that fluorescence-stained exosomes are delivered into human dermal fibroblasts (green: exosomes delivered into cells; blue: cell nuclei; and red: cell membranes).

Example 2: Evaluation of Delivery Ability of *Galactomyces*-Derived Exosomes into Dermal Fibroblasts In order to examine whether the *Galactomyces*-derived exosomes would be delivered into human dermal fibroblasts (purchased from CEFO Co., Ltd.), the following analysis was performed. To fluorescence-stain the membrane of the *Galactomyces*-derived exosomes prepared in Example 1, the exosomes were allowed to react with PKH67 fluorescence dye (purchased from Sigma-Aldrich). After the reaction, the reaction solution was fractionated with an MW3000 column (purchased from ThermoFisher Scientific) to remove free PHK67 that was not stained in the exosome membrane. A negative control was prepared by allowing PKH67 fluorescence dye to react with a buffered solution and fractionating the reaction product with the MW3000 column. The exosomes stained with PKH67 were incubated with pre-cultured human dermal fibroblasts, and then whether the exosomes would be delivered into the cells over time was observed using a fluorescence microscope. Hoechst fluorescence dye (purchased from Sigma-Aldrich) was used to stain the cell nuclei, and CellMask Orange Plasma Membrane Stain fluorescence dye was used to stain the cell membranes. As a result of examining whether the exosomes would be delivered into the cells, it was confirmed that the fluorescence-stained exosomes were delivered into the cells and green fluorescence accumulated in the cells over time (FIG. 3).

Example 3: Evaluation of Effect of Stimulating Collagen Production

Figure 4A:
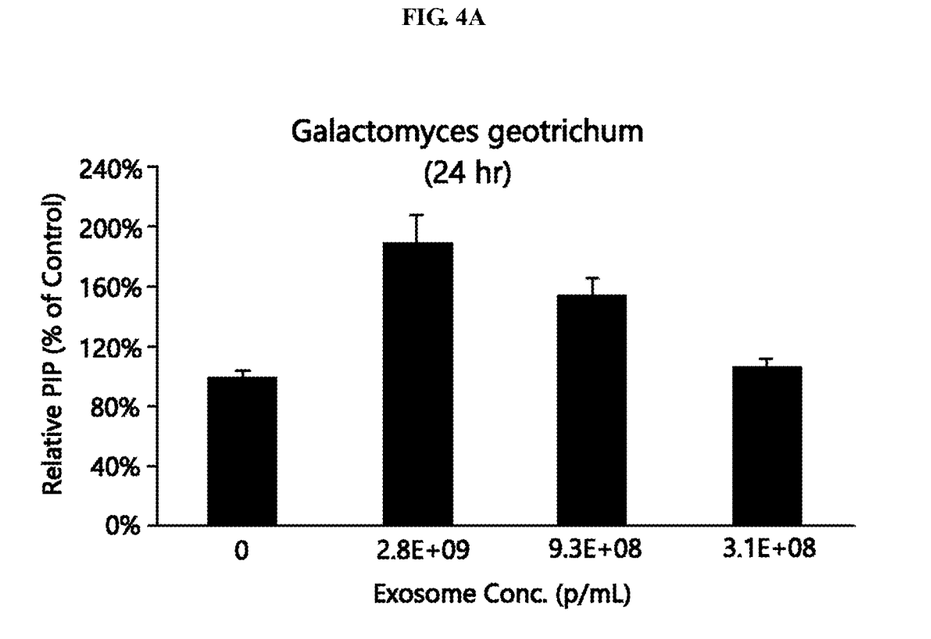
FIG. 4A and FIG. 4B depict graphs showing the relative collagen amount that increased when human dermal fibroblasts were treated with various concentrations of *Galactomyces*-derived exosomes and then cultured for 24 hours.
Figure 4B:
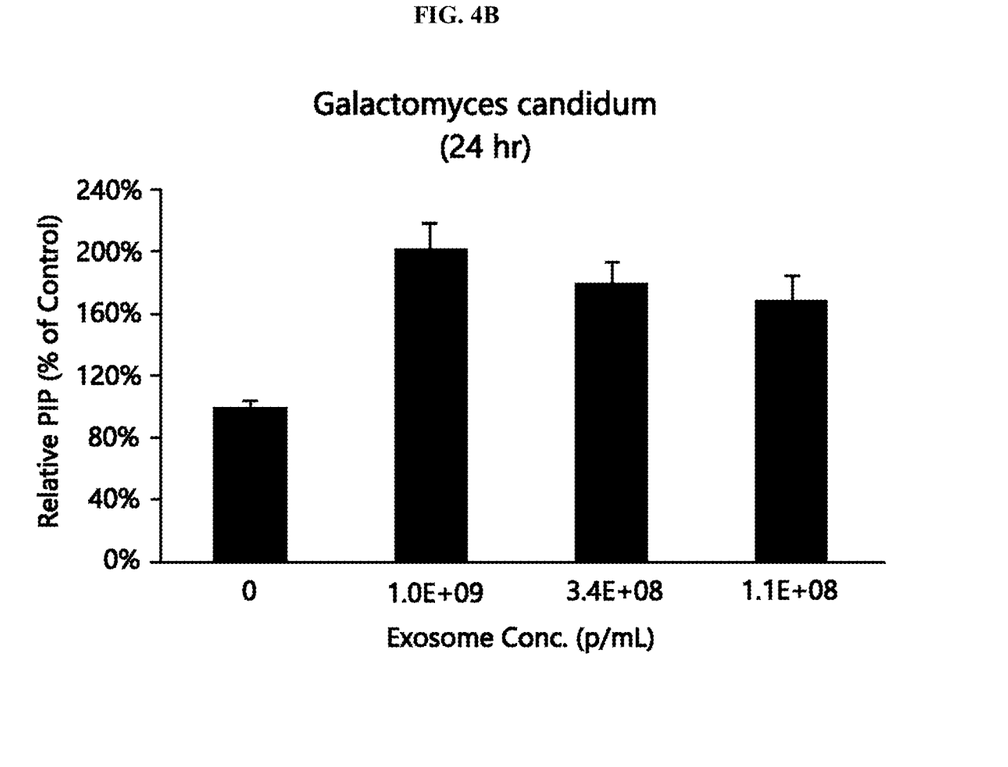

Human dermal fibroblasts (purchased from CEFO Co., Ltd.) dispersed in DMEM medium containing fetal bovine serum were dispensed into a multiwell plate, and then cultured for 24 hours and additionally cultured for 24 hours in serum-free medium. Thereafter, the *Galactomyces*-derived exosomes prepared in Example 1 were diluted in serum-free medium at various concentrations, and then the human dermal fibroblasts were treated with each of the dilutions and cultured. Thereafter, the culture media were collected and centrifuged, and then the centrifuged media were prepared. The amount of collagen, which was synthesized from the human dermal fibroblasts and accumulated in the culture media, was measured using an EIA kit (purchased from Takara Bio) for procollagen type I C-peptide (PIP). The total protein amount of the cell lysate was measured with a BCA Protein Assay Kit (purchased from ThermoFisher Scientific). The amount of collagen was normalized by the total protein amount and the relative amount of collagen was calculated. As a result of measuring the amount of collagen after 24 hours of culturing the human dermal fibroblasts treated by the *Galactomyces*-derived exosomes, it was confirmed that the *Galactomyces*-derived exosomes dose-dependently increased collagen synthesis in the human dermal fibroblasts (FIGS. 4A and 4B).

In addition, the filtered conditioned media of *Galactomyces* prepared in Example 1 were diluted in serum-free medium to concentrations of 20%, 6% and 2%, and then human dermal fibroblasts were treated with each of the dilutions and cultured. Further, the *Galactomyces*-derived exosomes prepared in Example 1 were diluted in serum-free medium at various concentrations, and then human dermal fibroblasts were treated with each of the dilutions and cultured. In the case of *Galactomyces geotrichum*, the concentrations of the *Galactomyces*-derived exosomes treated to the human dermal fibroblasts were $2.8 \times 10^9$ particles/mL (corresponding to 20% filtered conditioned media of *Galactomyces geotrichum*), $1.0 \times 10^9$ particles/mL (corresponding to 7.1% filtered conditioned media of *Galactomyces geotrichum*), and $3.0 \times 10^8$ particles/mL (corresponding to 2.0% filtered conditioned media of *Galactomyces geotrichum*), respectively. In the case of *Galactomyces candidum*, the concentrations of the *Galactomyces*-derived exosomes treated to the human dermal fibroblasts were $4.5 \times 10^9$ particles/mL (corresponding to 20% filtered conditioned media of *Galactomyces candidum*), $1.0 \times 10^9$ particles/mL (corresponding to 4.5% filtered conditioned media of *Galactomyces candidum*), and $3.0 \times 10^8$ particles/mL (corresponding to 1.3% filtered conditioned media of *Galactomyces candidum*), respectively. As a result of measuring the amount of collagen after 48 hours of culturing the human dermal fibroblasts treated by the *Galactomyces*-derived exosomes, it was confirmed that the *Galactomyces*-derived exosomes dose-dependently increased collagen synthesis in the human dermal fibroblasts (FIGS. 5A and 5B).

Figure 5A:
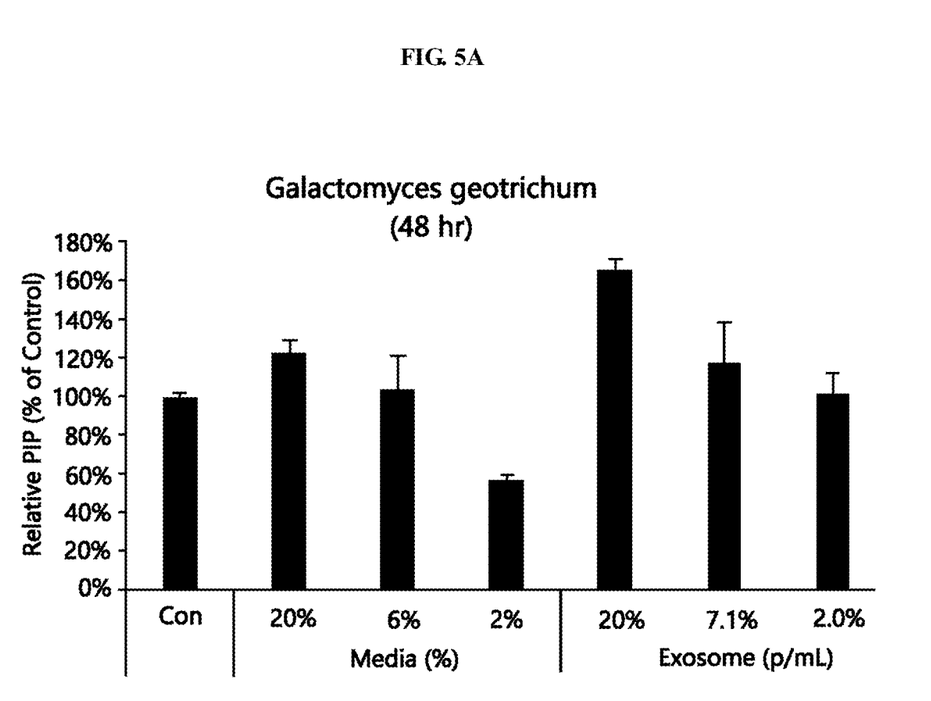
FIG. 5A and FIG. 5B depict graphs showing the relative collagen amount that increased (or decreased) when human dermal fibroblasts were treated with various concentrations of *Galactomyces*-derived exosomes or filtrates of conditioned media of *Galactomyces* and then cultured for 48 hours.
Figure 5B:
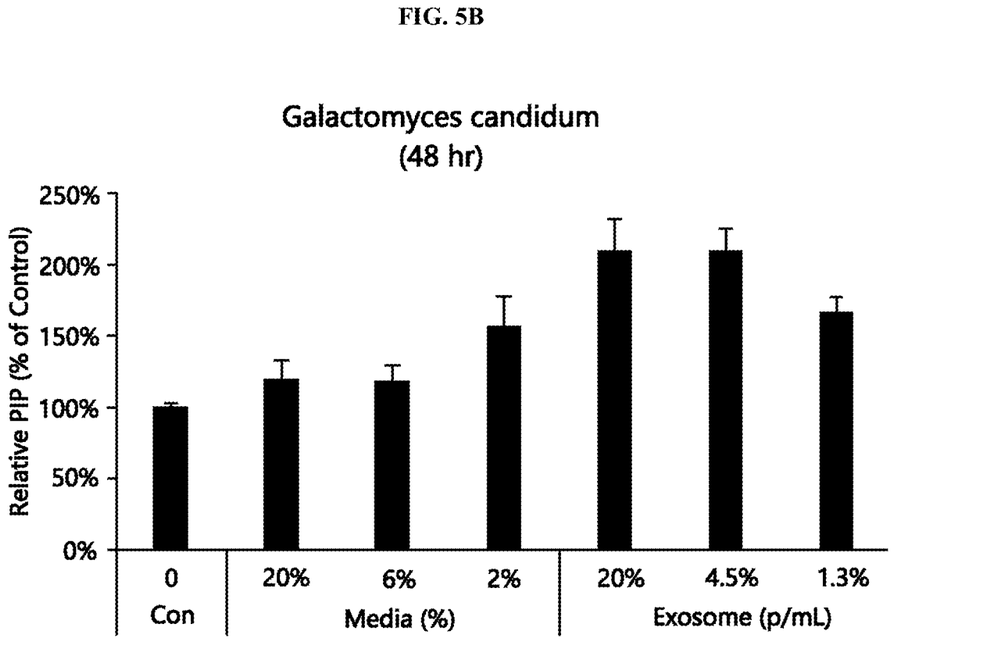

In the case of *Galactomyces geotrichum*, treatment with $2.8 \times 10^9$ particles/mL of the *Galactomyces*-derived exosomes (corresponding to 20% filtered conditioned media of *Galactomyces geotrichum*) showed a remarkable increase in collagen synthesis, as compared with treatment with 20% filtered conditioned media of *Galactomyces geotrichum*, and treatment with 2% filtered conditioned media of *Galactomyces geotrichum* rather inhibited collagen synthesis (FIG. 5A).

In the case of *Galactomyces candidum*, treatment with $1.0 \times 10^9$ particles/mL of the *Galactomyces*-derived exosomes (corresponding to 4.5% filtered conditioned media of *Galactomyces candidum*) showed a remarkable increase in collagen synthesis, as compared with treatment with 6% filtered conditioned media of *Galactomyces candidum*, although the concentration of the *Galactomyces*-derived exosomes expressed in terms of conditioned media was lower than 6% filtered conditioned media of *Galactomyces candidum*. Further, treatment with $4.5 \times 10^9$ particles/mL of the *Galactomyces*-derived exosomes (corresponding to 20% filtered conditioned media of *Galactomyces candidum*) showed a remarkable increase in collagen synthesis, as compared with 20% filtered conditioned media of *Galactomyces candidum*. Furthermore, treatment with $3.0 \times 10^8$ particles/mL of the *Galactomyces*-derived exosomes (corresponding to 1.3% filtered conditioned media of *Galactomyces candidum*) showed an increase in collagen synthesis, as compared with treatment with 2% filtered conditioned media of *Galactomyces candidum*, although the concentration of the *Galactomyces*-derived exosomes expressed in terms of conditioned media was lower than 2% filtered conditioned media of *Galactomyces candidum*.

According to the above results, it was confirmed that the cosmetic composition for skin regeneration, skin elasticity improvement or skin wrinkle reduction containing *Galactomyces*-derived exosomes as an active ingredient has a useful functional activity as a functional cosmetic composition (i.e., an activity of remarkably increasing collagen synthesis), as compared with filtrates of conditioned media of *Galactomyces*. Therefore, the *Galactomyces*-derived exosomes of the present invention are useful as an active ingredient for a functional cosmetic composition.

Although the present invention has been described with reference to the embodiments, the scope of the present invention is not limited to these embodiments. Any person skilled in the art will appreciate that various modifications and changes are possible without departing from the spirit and scope of the present invention and these modifications and changes also fall within the scope of the present invention.

We claim:

1. A method for skin regeneration, skin elasticity improvement or skin wrinkle reduction, the method comprising
   treating a skin of a subject in need thereof with a composition, wherein the composition comprises isolated exosomes derived from *Galactomyces* as an active ingredient, said exosomes excluding exosomes isolated from *Galactomyces* ferments,
   wherein the treating the skin with the composition promotes collagen production in the skin.

2. The method of claim 1, wherein the exosomes are isolated from conditioned media of *Galactomyces*.

3. The method of claim 1, wherein the composition is used in at least one form selected from the group consisting of a patch, a mask pack, a mask sheet, a cream, a tonic, an ointment, a suspension, an emulsion, a paste, a lotion, a gel, an oil, a spray, an aerosol, a mist, a foundation, a powder, and an oilpaper.

4. The method of claim 3, wherein the composition is applied to or soaked in at least one surface of the patch, the mask pack, or the mask sheet.

5. The method of claim 1, wherein the composition is a cream or a lotion.

6. The method of claim 1, wherein the subject is at least one selected from the group consisting of humans, dogs, cats, rodents, horses, cattle, monkeys and pigs.

7. A method for skin regeneration, skin elasticity improvement or skin wrinkle reduction, the method comprising steps of:
   (a)(a1) applying a composition comprising isolated exosomes derived from *Galactomyces* as an active ingredient to a skin of a subject in need thereof, wherein the exosomes exclude exosomes isolated from *Galactomyces* ferments; or (a2) contacting or attaching a patch, a mask pack or a mask sheet, which has the composition applied thereto or soaked therein, to the skin; or (a3) sequentially performing (a1) and (a2); and
   (b) leaving the composition on the skin for a period of time sufficient to promote collagen production in the skin.

8. The method of claim 1, wherein the exosomes are isolated from conditioned media of *Galactomyces*.

9. The method of claim 7, wherein the composition is a lotion or a cream in step (a).

10. The method of claim 7, further comprising step (c) removing the patch, the mask pack or the mask sheet from the skin after step (b), and applying the composition to the skin.

11. The method of claim 10, wherein the composition is a lotion or a cream in step (c).

12. The method of claim 7, wherein the composition is used in at least one form selected from the group consisting of a patch, a mask pack, a mask sheet, a cream, a tonic, an ointment, a suspension, an emulsion, a paste, a lotion, a gel, an oil, a spray, an aerosol, a mist, a foundation, a powder, and an oilpaper.

13. The method of claim 12, wherein the composition is applied to or soaked in at least one surface of the patch, the mask pack, or the mask sheet.

14. The method of claim 7, wherein the subject is at least one selected from the group consisting of humans, dogs, cats, rodents, horses, cattle, monkeys and pigs.

\* \* \* \* \*